United States Patent
Temple et al.

(10) Patent No.: US 8,409,512 B2
(45) Date of Patent: Apr. 2, 2013

(54) METHOD AND APPARATUS FOR USE OF REACTED HYDROGEN PEROXIDE COMPOUNDS IN INDUSTRIAL PROCESS WATERS

(75) Inventors: Stephen R. Temple, Santa Cruz, CA (US); Michael J. Stoltz, Duncansville, PA (US)

(73) Assignee: Steen Research, LLC, West Linn, OR (US)

(*) Notice: Subject to any disclaimer, the term of this patent is extended or adjusted under 35 U.S.C. 154(b) by 0 days.

(21) Appl. No.: 12/890,268

(22) Filed: Sep. 24, 2010
(Under 37 CFR 1.47)

(65) Prior Publication Data
US 2011/0104012 A1    May 5, 2011

Related U.S. Application Data

(60) Continuation of application No. 12/478,603, filed on Jun. 4, 2009, now Pat. No. 7,815,879, which is a continuation of application No. 11/442,554, filed on May 26, 2006, now Pat. No. 7,550,123, which is a continuation-in-part of application No. 10/704,238, filed on Nov. 7, 2003, now Pat. No. 7,112,309, which is a division of application No. 09/797,859, filed on Mar. 2, 2001, now Pat. No. 6,645,450.

(60) Provisional application No. 60/186,694, filed on Mar. 3, 2000.

(51) Int. Cl.
*B01D 53/34* (2006.01)
*B01D 53/14* (2006.01)

(52) U.S. Cl. .......... 422/120; 423/210; 95/154; 96/296; 96/234; 96/235

(58) Field of Classification Search .......... 96/296; 423/238, 245, 224; 422/120
See application file for complete search history.

(56) References Cited

U.S. PATENT DOCUMENTS

| | | | | | |
|---|---|---|---|---|---|
| 3,969,479 | A | * | 7/1976 | Lonnes et al. | 423/210 |
| 4,002,722 | A | * | 1/1977 | Suzuki et al. | 423/238 |
| 4,307,067 | A | * | 12/1981 | Tagawa et al. | 423/224 |
| 4,443,342 | A | * | 4/1984 | Stas et al. | 210/759 |
| 4,460,552 | A | * | 7/1984 | Zakrzewski | 423/210 |
| 4,595,577 | A | * | 6/1986 | Stas et al. | 423/245.2 |
| 5,485,728 | A | * | 1/1996 | Dickinson | 60/648 |
| 6,183,708 | B1 | * | 2/2001 | Hei et al. | 423/210 |
| 6,824,675 | B2 | * | 11/2004 | Boyer et al. | 208/146 |
| 6,926,878 | B2 | * | 8/2005 | Santina | 423/565 |
| 7,998,446 | B2 | * | 8/2011 | Pfeffer et al. | 423/243.01 |
| 2003/0056648 | A1 | * | 3/2003 | Fornai et al. | 95/65 |
| 2003/0094099 | A1 | * | 5/2003 | Lin et al. | 95/149 |
| 2008/0264250 | A1 | * | 10/2008 | Pfeffer et al. | 95/11 |

* cited by examiner

*Primary Examiner* — Duane Smith
*Assistant Examiner* — Ives Wu
(74) *Attorney, Agent, or Firm* — Owens Tarabichi LLP

(57) ABSTRACT

Methods and apparatuses are described for contacting an oxidizing solution such as an aqueous hydrogen peroxide composition of hydrogen peroxide and at least one additive that catalyzes the decomposition of the hydrogen peroxide into hydroxyl radicals with an atmospheric effluent containing odorous and/or noxious components. These components are absorbed by the aqueous hydrogen peroxide composition to produce an atmospheric effluent having reduced amounts of the odorous and/or noxious components. Various methods are described for adding the hydrogen peroxide and the decomposition additive.

20 Claims, 5 Drawing Sheets

US 8,409,512 B2

METHOD AND APPARATUS FOR USE OF REACTED HYDROGEN PEROXIDE COMPOUNDS IN INDUSTRIAL PROCESS WATERS

CROSS-REFERENCES TO RELATED APPLICATIONS

This application is a continuation of U.S. application Ser. No. 12/478,603 filed Jun. 4, 2009 now U.S. Pat. No. 7,815,879, which is a continuation of U.S. application Ser. No. 11/442,554 filed May 26, 2006, now U.S. Pat. No. 7,550,123, which is a continuation-in-part application of U.S. application Ser. No. 10/704,238 filed Nov. 7, 2003, now U.S. Pat. No. 7,112,309, which is a divisional of U.S. application Ser. No. 09/797,859 filed on Mar. 2, 2001, now U.S. Pat. No. 6,645,450, which claims the benefit of U.S. Provisional Patent Application No. 60/186,694, filed Mar. 3, 2000, all of which are incorporated by reference herein in their entireties.

BACKGROUND

1. Background of the Invention

This invention relates to the use of hydrogen peroxide reacted with strong reducing agents or stronger oxidizing agents to produce hydroxyl radicals. More specifically, the invention relates to utilizing in-situ generation of hydroxyl radicals to effectively oxidize odor and/or noxious compounds found in the food processing industry, such as poultry, beef, or fish processing, as well as rendering of meat, fish, or fowl by-products. This invention also relates to the use of hydroxyl radicals in the reduction of volatile organic compounds in aqueous gas scrubbers.

2. Description of Related Art

In the processing of poultry, beef, and fish, the large volume of organic material processed, as well as secondary processing (rendering), can generate large quantities of odiferous gases including organic sulfides, thiols, amines, alcohols, inorganic sulfides, ammonia, and simple carboxylic acids. These compounds are usually the result of biological action on the organic materials being processed. The odors produced are offensive and can travel significant distances to surrounding real estate. In other industries, such as chemical processing, paint production, wastewater treatment, etc., noxious compounds, such as volatile organic compounds (VOCs), are produced and are subject to environmental air quality regulations.

These gases are usually captured by a water media in air scrubber systems. In an air scrubber system, typically, air from the processing step is evacuated into a tower where water, broken into droplets either by contact with mixed media or distribution channels, absorbs the odiferous and noxious gas compounds. This water is recirculated and discharged typically to wastewater treatment systems. U.S. Pat. No. 6,015,536 to Lokkesmoe et al., provides a detailed description of the available air scrubbing systems on the market and is hereby incorporated by reference herein.

It can readily be seen that the scrubbing water media will quickly saturate with the offensive gases and lose its absorbing potential. At this point, the water has an intense disagreeable odor. Additives are commonly injected into the scrubbing water stream to reduce the odor content of the aqueous scrubbing media. The water is either dumped to the wastewater treatment facility or a portion is withdrawn to the wastewater facility and fresh makeup water is added to account for the difference.

It can also be seen that as the water saturates with gases, particularly nitrogen-bearing gases (ammonia), the pH of the water will rise proportionally. This marked increase in pH reduces the solubility of the gases causing them to flash to the atmosphere. This results in a decrease in the efficiency of the gas transfer to the water media.

Numerous attempts have been made to reduce the odor components in the air scrubbing system. Some technologies attempt to reduce the odor by injecting a maskant, which is a stronger, more pleasing odor compound. These maskants are extremely expensive, and the duration of the effectiveness is very short. These compounds do nothing to the actual structure of the odor molecule.

Maskants are also "fogged" or injected into spray orifices under high pressure to create a small droplet mist effect. These misted materials are directed into the atmosphere around the odor causing process. The misted materials either mask the odor or combine with the odor-causing molecule in the atmosphere to temporarily lower the offensive odor. These compounds, which are usually essential oils, are then blown with the prevailing winds. These materials are limited by extreme cost and do nothing to actually affect the odor-causing molecule.

U.S. Pat. Nos. 4,443,342 and 4,595,577, to Stas et al., describe a treatment method using hydrogen peroxide and copper sulfate as the catalyst for treatment of wastewater and gases containing organic sulfur compounds in a pH range below 6.5. It is well known to those of skill in the art that the efficiency of hydrogen peroxide as an oxidizer is increased in the pH range of 3 to 6.5. Stas et al. also describe using hydrogen peroxide in acidic aqueous media with 1 to 5 ppm of ferric sulfate as a catalyst when comparing the efficacy of the use of copper. This catalyst choice, in the amount used, only increases the efficiency of the hydrogen peroxide and does not effectively reduce the hydrogen peroxide to free radicals in the quantities that would be needed to oxidize odor components to soluble compounds to enable their removal.

Hydrogen peroxide by itself has only moderate success in air scrubbing systems. It reacts very slowly and is limited in the number of organic molecules it can oxidize. Some odor reduction can be achieved using hydrogen peroxide, but it is usually via microbiological control or an increase in oxygen content of the aqueous scrubbing media.

Halogen donors such as chlorine dioxide, chlorine gas, sodium hypochlorite, and hypobromous acids have had limited success in the art. The low electronegativity of these halogens (1.0 to 1.7 volts) limits their ability to oxidize odor constituents down to simple soluble compounds. Therefore their odor removal efficiency is low compared to the quantity needed. The use of halogen donors is falling under environmental scrutiny due to the formation of haloamines as well as trihalomethanes. Use of these halogens in aqueous streams eventually contributes to trihalomethanes and haloamines in surface waters.

U.S. Pat. No. 6,015,536, to Lokkesmoe et al, describes the use of peroxyacid compounds at a pH of 3 to 6 for odor reduction in air scrubbers. Peroxyacid, namely peracetic acid, is used as an oxidizer of odor causing molecules, and a reduction of odors from 5 to 50% is described. However, the large doses of peracetic acid needed preclude higher odor removal rates due to cost as well as the contribution of a pungent odor from the acetic and peracetic acids. The peracid compounds also lack sufficient electronegative potential to break up odor causing compounds to the degree needed for greater than 50% removal rates.

Ozone has been used with limited success in aqueous gas scrubbers. Ozone has an inherent high capital expenditure cost and is difficult to utilize the ozone gas in aqueous media. It is difficult to force enough gas into contact with the aqueous media to effectively oxidize odor compounds into simple soluble reduced-odor compounds. Ozone is also characterized by large electric utility costs associated with corona discharge type ozone production units.

Inorganic percompounds, such as percarbonates, persulfates, perborates, and permangenates, have demonstrated odor control potential. These compounds, however, are notoriously slow to liberate oxygen in cold water at elevated pH.

There exists a need in the art for a treatment process that has a high enough electronegative potential to reduce substantially all odor and/or noxious compounds to simple, soluble, reduced-odor/noxious, or odor/noxious-free compounds. This treatment process would offer even greater advance in the art if the process could also eliminate or greatly reduce the high cost of treating the scrubber water effluent in the wastewater treatment process.

SUMMARY OF THE INVENTION

In general, the present invention relates to chemical compositions and systems, including processes and equipment for removing odor and/or noxious components from an atmospheric effluent. In one embodiment, the chemical composition includes an oxidizer capable of oxidizing the odor and/or noxious components. In another embodiment, the chemical composition includes an aqueous hydrogen peroxide composition of hydrogen peroxide and an additive that catalyzes the decomposition of hydrogen peroxide into hydroxyl radicals. When contacted with the atmospheric effluent, the oxidizer or aqueous hydrogen peroxide composition oxidizes the odor and/or noxious components to produce an atmospheric effluent having reduced amounts of the odor component and/or noxious component and, in some embodiments, a non-odor offensive, environmentally acceptable by-product.

A method is described for removing at least one of an odor component and a noxious component from an atmospheric effluent. In one embodiment, the atmospheric effluent is contacted with a solution comprising an oxidizer. In another embodiment, the atmospheric effluent is contacted with an aqueous hydrogen peroxide composition including hydrogen peroxide and at least one additive that catalyzes the decomposition of the hydrogen peroxide to produce hydroxyl free radicals. The odorous and/or noxious component in the atmospheric effluent is absorbed by the oxidizer solution or the aqueous hydrogen peroxide composition and oxidized. In another embodiment, the method further comprises contacting the gas and liquid in a counter-current fashion. In another embodiment, the oxidizer solution or the aqueous hydrogen peroxide composition can be collected after contacting the gas in a tank and recycled via a recycle stream to again contact the gas. In this embodiment, additional oxidizer or additional hydrogen peroxide and decomposition additive may be added to the recycle stream as required or based upon measurement of a given solution parameter that is used to indicated whether additional oxidizer or additional hydrogen peroxide or decomposition additive is required. In some embodiments, the measurement of the solution parameter may be done continuously, periodically, or manually. In some embodiments, the addition of the oxidizer or other additives may be done automatically using a flow control valve based upon the measured value of the solution parameter to provide a more precise addition rate of these components and better control of the solution composition compared to a simple on/off valve.

In some embodiments, the decomposition additive comprises a metal-based compound, such as a ferrous or ferric salt, such as ferrous sulfate or ferric sulfate. In other embodiments, the decomposition additive comprises ozone, which may be added concurrently with the hydrogen peroxide to the liquid stream to improve contacting between the ozone gas and the hydrogen peroxide in the liquid stream.

In one embodiment, the method for removing an odorous or noxious component from a gas stream comprises adding hydrogen peroxide, a hydrogen peroxide decomposition additive, and a chelating agent to a liquid stream; contacting a gas stream comprising at least one odorous or noxious component with the liquid stream; and absorbing at least a portion of said odorous or noxious component in the gas stream into the liquid stream. The chelating agent is added to increase the solubility of the hydrogen peroxide decomposition additive. In some embodiments, the chelating agent allows the pH of the liquid stream to be controlled at a higher value than the liquid stream would otherwise have under similar operating conditions without the chelating agent. This may improve removal of certain odorous or noxious components. In some embodiments, the decomposition additive comprises a ferrous salt, such as ferrous sulfate, and the chelating agent comprises aminopolycarboxylates, such as nitrilotriacetic acid and hydroxyethyliminodiacetic acid; N-heteroxcyclic carboxylates, such as picolinic acid; polyhydroxy aromatics, such as gallic acid; or other compounds, such as rhodizonic acid, tetrahydroxy-1,4-quinone, and hexaketocyclohexane.

In some embodiments the pH of chemical composition or the liquid stream may be controlled at a select pH by adding acid or base directly to the liquid stream or to a tank that collects the liquid stream after contacting the gas. In other embodiments, the acid or base may be mixed with the decomposition additive before addition to the chemical composition or the liquid stream or the tank that collects the liquid stream after contacting the gas.

Other advantages of the present invention will become apparent from the following detailed description taken in conjunction with the accompanying drawings that illustrate, by way of example, the principles of the invention.

DETAILED DESCRIPTION OF THE INVENTION

Figure 1:
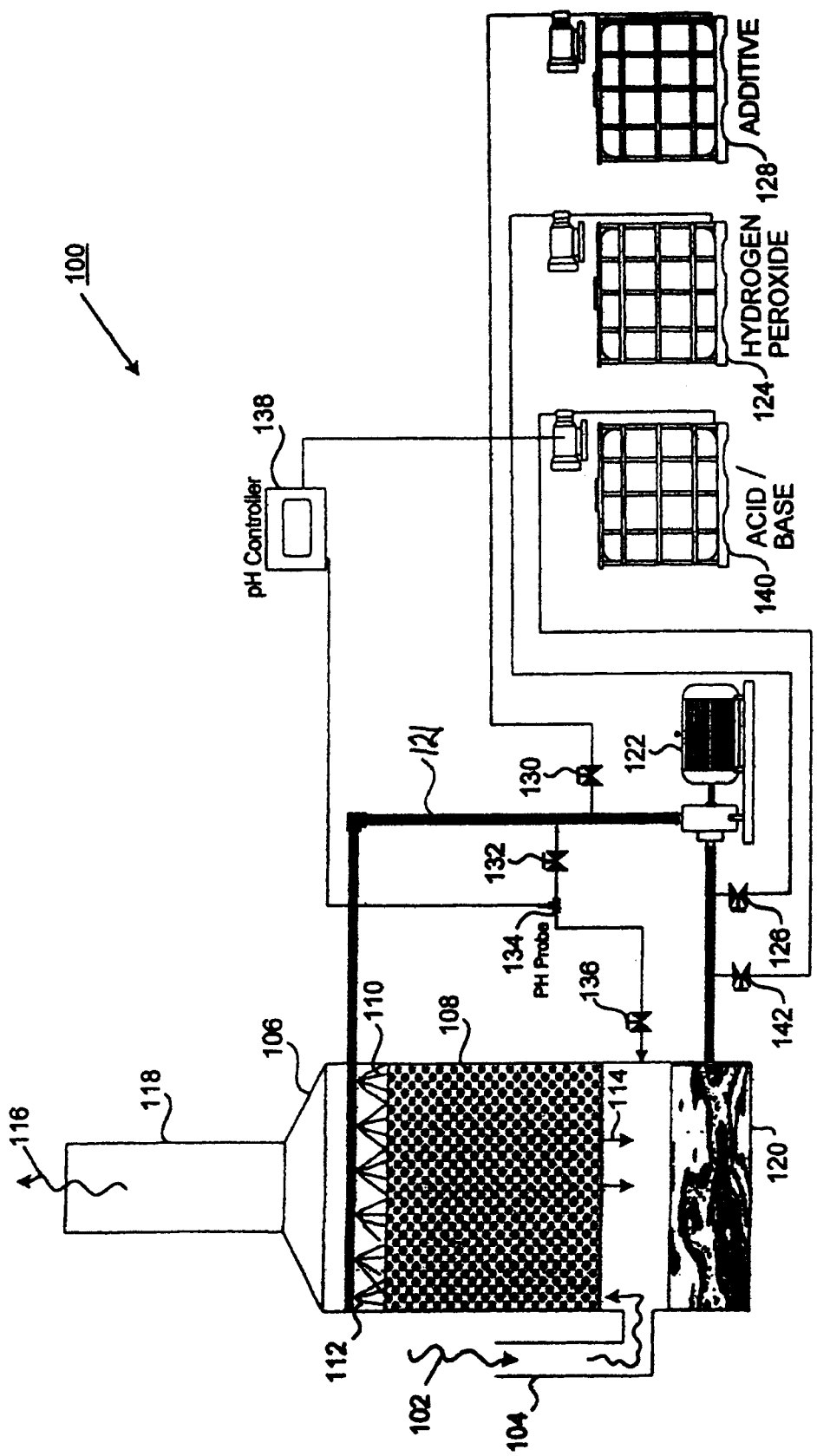
FIG. 1 shows a diagram of one embodiment of a process for removing an odor and/or noxious component from an atmospheric effluent.

The present invention will now be more fully described with reference to the accompanying drawings. To facilitate explanation, the invention will be described primarily in the context of a particular embodiment, namely, a wet scrubber system comprising a packed column. While the invention will be described in conjunction with this particular embodiment, it should be understood that the invention can be applied to a wide variety of applications, and it is intended to cover alternatives, modifications, and equivalents as may be included within the spirit and scope of the invention as defined by the appended claims. Accordingly, the following description is exemplary in that several embodiments are described (e.g., by use of the terms "preferably" or "for example"), but this description should not be viewed as limiting or as setting forth the only embodiments of the invention, as the invention encompasses other embodiments not specifically recited in this description. Further, the use of the term "invention" throughout this description is used broadly and is not intended to mean that any particular portion of the description is the only manner in which the invention may be made or used.

In general, the present invention uses a liquid stream or chemical composition comprising an oxidizer to oxidize absorbed odor and/or noxious components from an atmospheric gas stream. In some embodiments, additives may also be added to the liquid stream, including, for example, acid or base to control the pH of the liquid stream, additives to enhance the effectiveness of the oxidizer (e.g., when using hydrogen peroxide as the oxidizer the additive may be a hydrogen peroxide decomposition additive that catalyzes the decomposition of hydrogen peroxide to hydroxyl free radicals, chelating agents that, for example, increase the solubility of the hydrogen peroxide decomposition additive, wetting agents, and dispersants). It should be appreciated that any chemical added to the liquid stream may be referred to as an additive.

In one embodiment, the liquid stream comprises an aqueous hydrogen peroxide composition of hydrogen peroxide and at least one additive that serves to catalyze the rapid decomposition of the hydrogen peroxide into hydroxyl radicals. When contacted with an atmospheric effluent containing odor and/or noxious components, the hydroxyl radicals formed oxidize the odor and noxious components to a non-odor offensive, environmentally acceptable by-product. The by-product in combination with the aqueous hydrogen peroxide composition form a liquid effluent that provides charge neutralizing and adsorption species that, in addition, aid in treatment of wastewater effluents.

As can be seen in Table 1 below, the hydroxyl radical is known in the art as the second most electronegative species, second only to fluorine, and is significantly higher in oxidation potential than other compounds known in the art. The highly electronegative hydroxyl radical is, therefore, capable of a much greater decomposition of odor-causing molecules than any composition known in the art. Accordingly, it is not necessarily the intent of the invention to utilize the oxidation potential of the hydrogen peroxide but rather to utilize the hydroxyl radical produced from the decomposition of the hydrogen peroxide. It will be appreciated that in the decomposition of hydrogen peroxide some diatomic oxygen may also be produced, which also has an oxidation potential; however, the present invention is directed at utilizing the hydroxyl radical generated from the hydrogen peroxide decomposition. Accordingly, in one embodiment of the invention, at least a portion of the hydrogen peroxide in a solution used to contact atmospheric effluent containing odor and/or noxious components is decomposed to produce hydroxyl radical, which, in turn, oxidizes the odor and/or noxious components. In another embodiment, although not necessary, it is desirable to drive the hydrogen peroxide decomposition reaction to produce predominantly hydroxyl radicals to act in the oxidation of the odor and/or noxious components in the atmospheric effluent. It should be appreciated that neither all of the hydrogen peroxide needs to be decomposed to hydroxyl radicals nor does the decomposition need to result in only the production of hydroxyl radicals. In some embodiments, it is sufficient that a portion of the hydrogen peroxide decomposes to produce at least some quantity of hydroxyl radicals.

TABLE 1

| Oxidizer | Oxidation Potential (Volts) |
| --- | --- |
| fluorine | 3.0 |
| hydroxyl radical | 2.8 |
| ozone | 2.1 |
| hydrogen peroxide | 1.8 |
| potassium permanganate | 1.7 |
| hypobromous acid | 1.6 |
| chlorine dioxide | 1.5 |
| chlorine | 1.4 |

FIG. 1 shows a diagram of one embodiment of a process for removing an odor and/or noxious component from an atmospheric effluent. In this embodiment, a wet scrubber system is used to contact an atmospheric or gaseous effluent comprising an odorous or noxious component with an aqueous hydrogen peroxide composition comprising hydrogen peroxide and at least one additive that catalyzes the decomposition of the hydrogen peroxide to hydroxyl radicals. According to this embodiment, an atmospheric effluent 102 enters a packed scrubber 106 through an atmospheric effluent intake 104. The atmospheric effluent 102 may be from a food processing process, rendering process, or other industrial process that produces an atmospheric or gaseous effluent having odoriferous and/or noxious components. In this embodiment, the wet scrubber comprises a packed column 108. The atmospheric effluent 102 enters the packed column 108 where it is contacted with an aqueous hydrogen peroxide composition 110 supplied by dispenser(s) 112. The aqueous hydrogen peroxide composition 110 comprises hydrogen peroxide and at least one additive that catalyzes the decomposition of at least a portion of the hydrogen peroxide to hydroxyl radicals. In one embodiment, the aqueous hydrogen peroxide composition leaving dispenser(s) 112 has a relatively high concentration of hydroxyl radicals compared to a hydrogen peroxide solution without such an additive. In another embodiment, the additive catalyzes the decomposition to produce predominantly hydroxyl free radicals.

In the packed column 108, the atmospheric effluent 102 and the aqueous hydrogen peroxide composition 110 comprising hydroxyl free radicals contact each other, and the hydroxyl radicals oxidize the odorous and/or noxious components in the atmospheric effluent 102 to produce a substantially non-odor-offensive, environmentally-acceptable by-product that exits the packed column 108 with the aqueous hydrogen peroxide composition 110 as a liquid effluent 114. Dependent on the oxidation of the odor and/or noxious component, the liquid effluent 114 may contain by-product that is soluble in the aqueous hydrogen peroxide composition 110 or that may adsorb onto semi-colloidal particles formed in the aqueous hydrogen peroxide composition 110. The concentration of odorous and/or noxious components is reduced in the atmospheric effluent 102, which exits the packed column 108 as a gaseous exhaust effluent 116 by way of a vent 118.

The liquid effluent 114 exits the packed column 108 and is collected in a reservoir 120 for discharge to a wastewater facility. In some embodiments, the reservoir is integral to the scrubber or packed column 108, in which case, the reservoir 120 may also be vented. In some embodiments, the liquid effluent 114 may be collected and the entire reservoir 120 dumped into a waste treatment pathway or waste treatment facility. In other embodiments, the reservoir 120 may be equipped with an overflow system so that a portion of the liquid effluent 114 is continually or periodically overflowed into a waste treatment pathway for delivery to a waste treatment facility. In the latter case, the reservoir 120 may also have an add-back line to allow introduction of makeup water into the reservoir 120 so that a constant effluent level is maintained in the reservoir 120.

A recycle line or sidestream 121 in fluid communication with the reservoir 120 and the dispenser(s) 112 is used to transfer liquid effluent 114 from the reservoir back to the top of the packed column 108 by using a pump 122 within the recycle line 121. The fluid in this recycle line or sidestream 121 may be referred to as a recycle stream or fluid. Those of skill in the art will appreciate that a wide variety of pumps may be used. The pump should be chosen to provide sufficient power to move fluid at the mass flow rate required by the particular scrubber. It should also resist chemical attach by the liquid effluent and any additives present in the liquid effluent. For certain applications, it may be desirable to use specific types of pumps. For example, as described below, when using the pump to introduce ozone or other gaseous catalysts, a pump capable of introducing a gas into a liquid stream could be used, such as a regenerative turbine pump.

It will be appreciated that at the start of the process the contents of the reservoir 120 may be essentially makeup water until the process has completed several cycles in which the aqueous hydrogen peroxide composition 110 has been contacted with the atmospheric effluent 102. Aqueous hydrogen peroxide and any additives are added to the liquid effluent 114 in the recycle line or sidestream 121 to form the aqueous hydrogen peroxide composition 110, which is then delivered to the atmospheric effluent 102 in the packed column 108 via dispenser(s) 112.

The hydrogen peroxide in the aqueous hydrogen peroxide composition is delivered from a source container 124 into the recycle line or sidestream 121 via an inlet valve 126, which is positioned upstream of the pump 122. The concentration of hydrogen peroxide in the source container 124 should be chosen to allow safe handling given the equipment in use and to provide sufficient concentration for the needs of the scrubber. Although the concentration of hydrogen peroxide in the source container 124 may be selected within a wide range, specific embodiments will range between about 35% to 50% by weight in an aqueous solution as these ranges are currently industrially available and legally transportable. In a preferred embodiment, the concentration is about 50% by weight in aqueous solution.

At least one decomposition additive in the aqueous hydrogen peroxide composition is delivered from a source container 128 into the recycle line or sidestream 121 via an inlet valve 130, which is positioned downstream of the pump 122. Upon the addition of the additive on the downstream side of the pump 122, the decomposition of at least a portion of the hydrogen peroxide to hydroxyl radicals is catalyzed. In another embodiment, the decomposition produces predominantly hydroxyl radicals. As noted above, it is not necessary that all of the hydrogen peroxide decompose to hydroxyl radicals or that the decomposition itself only produce hydroxyl radicals. Depending upon the amount of hydroxyl radicals produced, which can be determined based upon the removal efficiency of the odorous and/or noxious components from the gas stream, the rate and amount of additive delivered to the system can be adjusted. Addition of the additive on the backstream or downstream side of the pump 122 is preferred over arrangements on the vacuum side as it reduces wear on the pump 122 from the decomposition product of hydrogen peroxide, e.g., the hydroxyl radicals. However, it should be appreciated that the additive may be added upstream of the pump 122 using a similar inlet valve. The aqueous hydrogen peroxide composition comprising the hydroxyl radicals is then delivered to the packing column 108 via dispensers 112 to contact the atmospheric effluent 102.

In some embodiments, the aqueous hydrogen peroxide composition may include additional additives, including additives that catalyze the decomposition of hydrogen peroxide, wetting agents, and/or chelating agents (discussed further below). Addition of these additives would be made similar to the addition of the additive for catalyzing the decomposition of the hydrogen peroxide discussed above. Thus, there may be separate source containers and inlet valves to enable the regulated delivery of these additional additives in aqueous form to the recycle or sidestream 121. Preferably, these additional additives are added on the downstream side of the pump 122; however, these additives could be added at other locations, including, for example, anywhere along the recycle line or sidestream 121 or directly to the reservoir 120. Additionally, some or all of the other additives, wetting agents, and/or chelating agents may be mixed together and delivered from a single source container. Alternatively, any one or more of these additives may be provided together with one or more other source materials. For example, the hydrogen peroxide in its source container 124 may contain any one or more chemically compatible (e.g., resistant to oxidation) additives such as certain chelating agents and/or wetting agents. Of course, the additives may also be provided with the decomposition additive from its source container 128 and/or from the source container 140 for the acid or base (discussed further below).

It will be appreciated that the inlet valves discussed in FIG. 1 are regulated so that the aqueous hydrogen peroxide composition in the recycle line or sidestream 121 has a desired composition. Regulation of the inlet valves may be by any means, such as a controller or formulator system, such that the individual components are delivered into the recycle or sidestream 121 in the desired amounts to form the aqueous hydrogen peroxide composition. Further, this system for feeding these components may stand-alone or be incorporated as part of a larger control system, particularly in the case where the system includes more than one scrubber. It will be appreciated that other embodiments may be utilized in which the components of the aqueous hydrogen peroxide composition are added at different locations within the system, including different locations along the recycle or sidestream 121 or directly to the reservoir 120.

One of skill in the art will appreciate that the actual composition of the aqueous hydrogen peroxide composition in the recycle line or sidestream 121 and, specifically, the concentration of hydrogen peroxide, the additive, and hydroxyl free radicals therein, is determined based upon the composition of the gas stream entering the scrubber and the specific gaseous components to be removed, as well as the scrubber operating conditions. At a given set of scrubber operating conditions (such as the gas flow rate and concentration of odorous and/or noxious components and the liquid flow rate through the scrubber), the addition rate of either or both of the hydrogen peroxide and the additive may be adjusted to provide the necessary production of hydroxyl free radicals to achieve the desired removal rate of odorous and/or noxious components. Of course, the concentration of the hydrogen peroxide and the additive in their respective source containers may be adjusted to achieve the desired rate of addition of each to the system in balance with overall water balance considerations.

The system and process of the embodiment of FIG. 1 may also include a pH control loop to measure the pH of the liquid effluent 114/aqueous hydrogen peroxide composition 110 in the recycle line or sidestream 121 and, in response, to regulate the addition of an acid or base into the recycle line or sidestream 121 to maintain the pH of that stream within a preferred pH range. In such an embodiment, an inlet valve 132 permits the withdrawal of a portion of the aqueous stream in the recycle line or sidestream 121. This stream contacts a pH probe 134 and passes back to the packed scrubber 106 or the reservoir 120. The pH probe 134 measures the pH of this stream and communicates the measured pH to a pH controller 138. The pH controller 138 then regulates, as needed, the addition of an acid or base from an acid or base source container 140 into the recycle line or sidestream 121 via an inlet valve 142. In one embodiment, the inlet valve 142 is located upstream of the inlet valve 126. In another embodiment, the acid or base is added to the stream withdrawn from the recycle line or sidestream 121 that contacts the pH probe (not shown). In this case, the acid or base would be added downstream of the pH probe before this stream is returned to the reservoir 120. In another embodiment, the acid or base can be added directly to the reservoir 120 (not shown).

Through the addition of acid or base using the pH control loop, the pH of the liquid effluent 114/aqueous hydrogen peroxide composition 110 in the recycle line or sidestream 121 is maintained at a level that maximizes the decomposition of the hydrogen peroxide by the additive(s) that catalyze such decomposition. This, in turn, allows the removal of the odor and/or noxious component from an atmospheric effluent to be optimized. One of skill in the art will appreciate that the optimal pH to be used will be dependent upon the particular gaseous component to be removed and oxidized and its properties and concentration in the atmospheric effluent, as well as the composition of the aqueous hydrogen peroxide composition and operating conditions of the scrubber. For example, in removing hydrogen sulfide, its solubility is pH dependent and increases with increasing pH above about pH 5 to about pH 9.5. Accordingly, this solubility property needs to be taken into account in selecting an operating pH. Additionally, the solubility of the decomposition additive, particularly a metal-based additive (discussed below), relative to the pH of the aqueous hydrogen peroxide composition needs to be taken into account. Typically, metal-based additives are less soluble at higher pH, so that the pH may need to be controlled at a lower level to maintain an adequate concentration of such an additive in solution and available to catalyze the decomposition of the hydrogen peroxide.

As described above, at least one additive is added to form, in conjunction with the added hydrogen peroxide, the aqueous hydrogen peroxide composition. This additive is used to catalyze the decomposition of hydrogen peroxide to hydroxyl free radicals. Generally, the catalyst source is chosen relative to the gas stream being treated and the specific gaseous components to be removed so as to generate an aqueous hydrogen peroxide composition having optimal concentrations of hydroxyl free radicals. The catalyst source is also selected with a view toward safety and effectiveness. Obviously, the concentration of the catalyst used will vary depending upon the particular catalyst chosen for the task. Typically, the catalyst will be delivered using an aqueous solution, although for some catalyses, such as ozone and certain of the group VII elements (discussed further below), a direct gaseous addition will be necessary.

In one embodiment, the additive used is ferrous sulfate. The use of ferrous sulfate in sufficient quantities to catalyze the decomposition of the hydrogen peroxide into hydroxyl radicals is well known to those of skill in the art as "Fenton's Reagent". However, the use of the highly electronegative hydroxyl radicals has not been explored in air scrubbers, such as those utilized in food processing and in other process industries that produce atmospheric effluents, such as rendering, containing odor and/or noxious components, for example, volatile organic compounds (VOCs).

In aqueous media, ferrous iron decomposes hydrogen peroxide in the following manner:

$$Fe^{2+} + H_2O_2 \rightarrow Fe^{3+} + OH^- + OH^*$$

As earlier described, the hydroxyl radical formed oxidizes the odor producing components and/or noxious components via electron transfer.

It should be appreciated that the solubility limit of the catalyst presents an upper bound on concentration of the catalyst in the source container. In the case of ferrous sulfate, the concentration may be selected within a wide range with specific embodiments within the range between about 20% to about 38% by weight in aqueous solution. In a preferred embodiment the concentration of ferrous sulfate is about 38% by weight in aqueous solution. In this embodiment, the aqueous hydrogen peroxide composition may be added as a 50% by weight hydrogen peroxide solution in its source container.

The ratio by weight of the hydrogen peroxide solution to the ferrous sulfate, based on a 50% by weight hydrogen peroxide solution and a 38% by weight ferrous sulfate solution should be within the range between about 1:1 to about 100:1, with a preferred ratio within the range between about 2:1 to about 50:1, and with a most preferred ratio within the range between about 5:1 to about 15:1. The higher the ferrous sulfate ratio the more the decomposition reaction is driven to producing hydroxyl free radicals. The ratio can be as high as one part 50% by weight hydrogen peroxide solution to ten parts 38% ferrous sulfate solution, but an extreme amount of heat is generated. While this amount of heat may be acceptable in some settings, it may not be desirable in others.

It should be appreciated that the use of highly electronegative hydroxyl radicals is capable of a much greater decomposition of odor-causing molecules than any composition known in the art. Further, the use of some of the decomposition additives, particularly, ferrous sulfate, not only reduces the hydrogen peroxide into the hydroxyl radicals but also introduces a semi-colloidal substrate into the aqueous media that is capable of effectively adsorbing odor-causing and/or noxious compounds.

As noted above, in some embodiments, additional additives may be added to the aqueous hydrogen peroxide composition, their choice depending on the particular system in which they will be used, cost, environmental concerns, and organic loading of the effluent being treated. These additional additives may include additional catalysts or other additives and may be added alone or in combination, such as wetting agents, dispersant polymers, and chelating agents.

Additives that act as catalysts, other than ferrous sulfate, may be used alone or in combination with ferrous sulfate. In one embodiment, the catalytic additive may be any element chosen from elements in groups 3B, 4B, 5B, 6B, 7B, 8B, 1B, and 2B of the Periodic Table of Elements and may include combinations thereof. It will be readily apparent to one of normal skill in the art that the additive(s) selected from these elements would be chosen based upon cost, speed of reaction and environmental impact. Among these elements, iron and its conjugates are the cheapest, most readily available, and are of lowest environmental impact.

More preferred are the "d" block transition elements, characterized by the "d" electrons in their valence shell, and combinations thereof. For example, the additive may be cobalt. In one embodiment, the aqueous hydrogen peroxide composition may be formed using an amount of cobalt within the range between about 0.5% wt/wt % to about 1% wt/wt % of the total aqueous hydrogen peroxide composition. Or, the amount of cobalt may be between about 0.5% wt/wt % to about 1% wt/wt % of a solution comprised of cobalt and a 50% by weight hydrogen peroxide solution. In another embodiment, the additive may be any element selected from elements in Group 7A of the Periodic Table of Elements and combinations thereof, for example, fluorine.

In one embodiment, the decomposition additive may be ozone. Using ozone as the additive to catalyze the decomposition of the hydrogen peroxide provides numerous advantages. In particular, using ozone allows for operation at higher pH because the ozone is not as solubility limited at higher pH compared to the decomposition additives that comprise metals. As discussed below, the solubility of a metal-based decomposition additive typically decreases at higher pH, but a chelating agent may be used to enhance its solubility. The use of ozone, however, may displace the need to use a chelating agent in combination with a metal-based decomposition, thereby allowing operation at higher pHs. As noted above, operation at higher pH provides the aqueous hydrogen peroxide composition with a greater capacity to absorb acidic odorous and noxious components in the gas stream to be treated, thereby increasing the removal efficiency of the process. Accordingly, when using ozone, because solubility of a metal-based catalytic additive is not an issue, the pH of the aqueous hydrogen peroxide composition may be increased. The particular pH used in operation can be determined as discussed above and is based upon factors such as the type and concentration of the odorous and/or noxious components in the gas stream and the operating conditions of the scrubber. Generally, it should be appreciated that virtually any pH above, for example, 5.0, may be used.

When using ozone very poor gas transfer to liquid media has been observed in the art. As part of the present invention, use of a regenerative turbine pump, for example, a Burks regenerative turbine pump manufactured by Burks Manufacturing, can be used as the pump for the recycle line or sidestream to provide sufficient to excellent mixing of the ozone with the liquid stream in the recycle line or sidestream. Referring back to FIG. 1, such a regenerative turbine pump can be used as the pump 122 in the recycle or sidestream 121. In this case, the hydrogen peroxide is added as shown in FIG. 1 upstream of or on the vacuum side of the regenerative turbine pump 121. An ozone/air mixture is then added to an inlet port pre-built on the vacuum side of the regenerative turbine pump 121. The resulting liquid discharged from the regenerative turbine pump 121 provides a well mixed stream. In particular, pressurizing the discharge side of the pump to a minimum of 100 psi by using a pinch valve (not shown) gives excellent gas transfer of the ozone to the liquid media in the recycle line or sidestream. In this instance, rather than the ozone being delivered through the inlet valve 130 used for other liquid phase additives, the ozone would instead be connected to the inlet port pre-built on the vacuum side of the regenerative turbine pump 122 and regulated through the pinch valve. It will be appreciated that this pinch valve may also be controlled using the same control system or formulator system that regulates the other inlet valves of FIG. 1. It should be appreciated that in some embodiments, the ozone may be added either upstream or downstream of the circulation pump or in any other manner to maximize the transfer of the ozone into the liquid phase and the decomposition of the hydrogen peroxide.

More particularly, as the liquid effluent 114, enriched with hydrogen peroxide (due to the addition of hydrogen peroxide from the hydrogen peroxide source container 124), enters the vacuum side of the regenerative turbine pump 122, the air/ozone mixture is introduced through a pre-machined air port. Intense shear is developed inside the regenerative turbine pump 122 that breaks the ozone/air mixture into microbubbles entrained in the liquid solution. The discharge from the regenerative turbine pump 122 is pressurized to a minimum of 100 psi through a pinch valve assembly, ensuring solubilization of the ozone into the liquid effluent 114 enriched with hydrogen peroxide. This allows for the efficient decomposition of the hydrogen peroxide by the ozone into hydroxyl radicals.

In another embodiment, a nonionic wetting agent may be added to the scrubber or to the aqueous hydrogen peroxide composition to enhance its activity by allowing further penetration of the oxidizing agent into crevices of bacterial forms of odor and/or noxious components. While the exact mechanism is not known, it is believed that certain nonionic surfactants, i.e., wetting agents, assist in the degradation of bacterial cell walls allowing the aqueous hydrogen peroxide composition to more readily kill the bacteria in the medium.

Preferred wetting agents are octylphenols, ethylene oxide block copolymers, propylene oxide block copolymers, and combinations thereof. The determining factors for wetting agent choice is organic loading of the effluent, i.e., the level of proteins or starches in the effluent, cleanliness of the system being treated, i.e., the amount of deposits and slime on the surfaces of the scrubber tank and packing, as well as need for defoaming capabilities.

In one embodiment, the wetting agent, as 100% active material, is present in an amount up to about 10% by weight of the aqueous hydrogen peroxide composition (in the scrubber or as additives to a scrubber sidestream), with a preferred embodiment being an amount up to about 5% by weight of the aqueous hydrogen peroxide composition, and in a most preferred embodiment an amount up to about 1% by weight of the aqueous hydrogen peroxide composition.

In another embodiment, a low molecular weight dispersant polymer may be added to the scrubber or to the aqueous hydrogen peroxide composition in order to prevent iron and other particle agglomeration in the aqueous media as well as to prevent iron and organic deposition in lower liquid flow areas. In one embodiment, the average molecular weight of these low molecular weight dispersants is within the range between about 1,000 to about 22,000, with a preferred average molecular weight within the range between about 1,000 to about 9,000. These low molecular weight dispersants may be, but are not limited to, homopolymers of acrylic acid, methacrylic acid, acrylamide, copolymers and terpolymers acrylates, methacrylates, acrylamide, AMPS (2-acrylamido-2-methyl propane sulfonic acid), and combinations thereof. For example, a dispersant resistant to oxidation may be desirable in situations where sulfur-based compounds that are formed as a result of operation at higher pHs and interaction with a metal-based decomposition additive in which insoluble agglomerations, such as zinc sulfate, are formed.

The low molecular weight dispersant polymer is added on a weight percent basis (i.e., wt/wt % on the total composition weight of the aqueous hydrogen peroxide composition in the scrubber or as additives to a scrubber sidestream). A preferred percentage of the low molecular weight dispersant, in the aqueous hydrogen peroxide composition, is within the range between about 0.5% active wt/wt % to about 10% active wt/wt % of the total aqueous hydrogen peroxide composition. A more preferred percentage is within the range between about 0.5% active wt/wt % to about 5% active wt/wt % of the total aqueous hydrogen peroxide composition, and a most preferred percentage is within the range between about 0.5% active wt/wt % to about 2% active wt/wt % of the total aqueous hydrogen peroxide composition.

In another embodiment, a chelating agent may be added to the aqueous hydrogen peroxide composition. As earlier discussed, a semi-collodial metal complex may form during the oxidation process, and in some instances, the development of this colloidal metal complex is undesirable. A chelating agent may be added to prevent the formation of metal hydroxides or other insoluble metal complexes. In one embodiment, the chelating agents may be organic acids such as gluconic acids, glycolic acids, lactic acids, and combinations thereof. It will be appreciated that a large number of chelating agents may also be used and their selection readily apparent to those of skill in the art; however, the chelating agent should not be of such potent chelating ability as to prevent the availability of the metal complex for decomposition purposes.

A chelating agent may also be added to enhance the solubility of the decomposition additive or catalysts. This may, in some embodiments, allows for operation at higher pH. As noted above, higher pH increases removal of the odorous and/or noxious components in the gas compared to lower pH operation. It should be appreciated, however, that a chelating agent may be used to enhance the solubility of the decomposition additive in some embodiments where increasing the pH may not be necessary.

Generally, chelating agents can be selected based upon the particular decomposition additive being used. For example, chelating agents known in the art may be used to increase the solubility of metal-based decomposition additives, such as ferrous ion and other metal complexes. In addition, ferric ($Fe^{3+}$) ion may be used as the decomposition additive to decompose hydrogen peroxide to produce hydroxyl radicals, and chelating agents may be added to increase the solubility of the ferric ion, thereby increasing the production of hydroxyl free radicals and allowing for operation at a higher pH. Chemical Treatment of Pesticide Wastes—Evaluation of Fe(III) Chelates for Catalytic Hydrogen Peroxide Oxidation of 2,4-D at Circumneutral pH, Sun et al., J. Agric. Food Chem, 1992, 40, 322-327, which is incorporated by reference herein, describes several chelating agents that may be used to solubilize ferric ion. Such chelating agents that showed "high" catalytic activity and that may be used in the present invention include: aminopolycarboxylates, such as nitrilotriacetic acid and hydroxyethyliminodiacetic acid; N-heteroxcyclic carboxylates, such as picolinic acid; polyhydroxy aromatics, such as gallic acid; and other compounds, such as rhodizonic acid, tetrahydroxy-1,4-quinone, and hexaketocyclohexane. These chelating agents may be used separately. However, it may be possible to use mixtures of these chelating agents as well.

It should be appreciated that the chelating agent and the decomposition additive, such as ferrous ion or ferric ion (which may be added, for example, as ferric sulfate) may be mixed before use to allow for chelation. For example, referring to FIG. 1, the chelating agent and the ferric ion may be chelated prior to placing such a mixture in the additive source container 128. In this case, the selection of the decomposition additive and chelating agent can be based upon the specific application or particular gaseous components to be removed and the desired operating pH. By mixing the decomposition additive and the chelating agent prior to use, this mixture is essentially "tailor-made" and is ready for immediate use in the particular application at issue. In fact, this mixture can be prepared remote from the facility where it will be used and shipped to that facility for immediate use.

Alternatively, the decomposition additive and the chelating agent may be added separately to the additive source container 128, thereby allowing for in-situ chelation in the source container 128. In this case, consideration must be given to the rate at which this solution is added through the valve 130 to the system to provide sufficient time for chelation to occur. One of skill in the art will appreciate the conditions necessary to chelate, including use of the proper pH, which may be, for example, pH 6. Alternatively still, the chelating agent may be added through the use of a separate source container (not shown) in a manner similar to that of the additive source container 128. Further, the use of a separate source container for the chelating agent may be used to dispense the chelating agent into the recycle line or sidestream either upstream or downstream of the pump 122; however, it is preferable to dispense the chelating agent into the recycle line or sidestream as closely as possible to the point where the additive is added to the recycle line or sidestream.

As noted above, use of a chelating agent to increase the solubility of the decomposition additive (for example metal-based additives and, in particular, ferrous or ferric ions) allows for operation at a higher pH in the aqueous hydrogen peroxide composition that is fed to the scrubber. Operation at higher pH increases the capacity of the aqueous hydrogen peroxide composition to absorb additional acidic gases, thereby increasing the removal efficiency of the process. It should be appreciated that the specific pH used will be dependent upon the particular gaseous components to be removed from the gas stream and, correspondingly, may include a wide range of pHs. In some embodiments, it may be desirable to not change the operating pH significantly or at all upon the addition of a chelating agent.

The present invention has been described above primarily with reference to removal of odor and/or noxious components from an atmospheric effluent in which the oxidized odor and/or noxious components are oxidized during contact with an aqueous hydrogen peroxide composition to produce a substantially non-odor offensive, environmentally acceptable by-product that is solubilized in or adsorbed into the aqueous hydrogen peroxide composition to form a liquid effluent. It should be appreciated, however, that various oxidizers or solutions containing oxidizers may be used. For example, oxidizing compounds such as chlorine gas, sodium hypochlorite, hypobromous acid, chlorine dioxide, hydrogen peroxide, peroxy acids, ozone, and permanganate may be used.

In addition, the present invention has been described above in the context of one embodiment: the use of a wet scrubber system using a single packed column with a single integrated reservoir. It should be appreciated that other gas/liquid contactors may be used in the wet scrubber system. For example, spray towers, Venture spray condensers, or a combination of spray towers and packed columns may be used. Further, counter-current scrubbers, where the direction of the gas flow is opposite the direction of the liquid flow; co-current scrubbers, where the direction of the gas flow is in the same direction as the liquid flow; and cross-flow scrubbers, where the direction of the gas flow is at an angle to the direction of the liquid flow; may be used. In addition, it should be appreciated that more than one reservoir may be used for a single scrubber or, alternatively, one reservoir may be used for more than one scrubber. Further, it should be appreciated that the reservoir does not necessarily need to be integral to the gas/liquid contactor and may be a separate tank, provided that appropriate gas seals are in place.

It should be appreciated that more than one gas/liquid contactor may be used in a single system. Such gas/liquid contactors may be of the same or various types and may be configured to operate in series or in parallel. Each gas/liquid contactor could also have its own reservoir or multiple gas/liquid contactors may share the same reservoir. In using more than one gas/liquid contactor with one or more reservoirs, it is possible to utilize one set of source containers for hydrogen peroxide, additives, and any acid or base required for pH control.

Figure 1A:
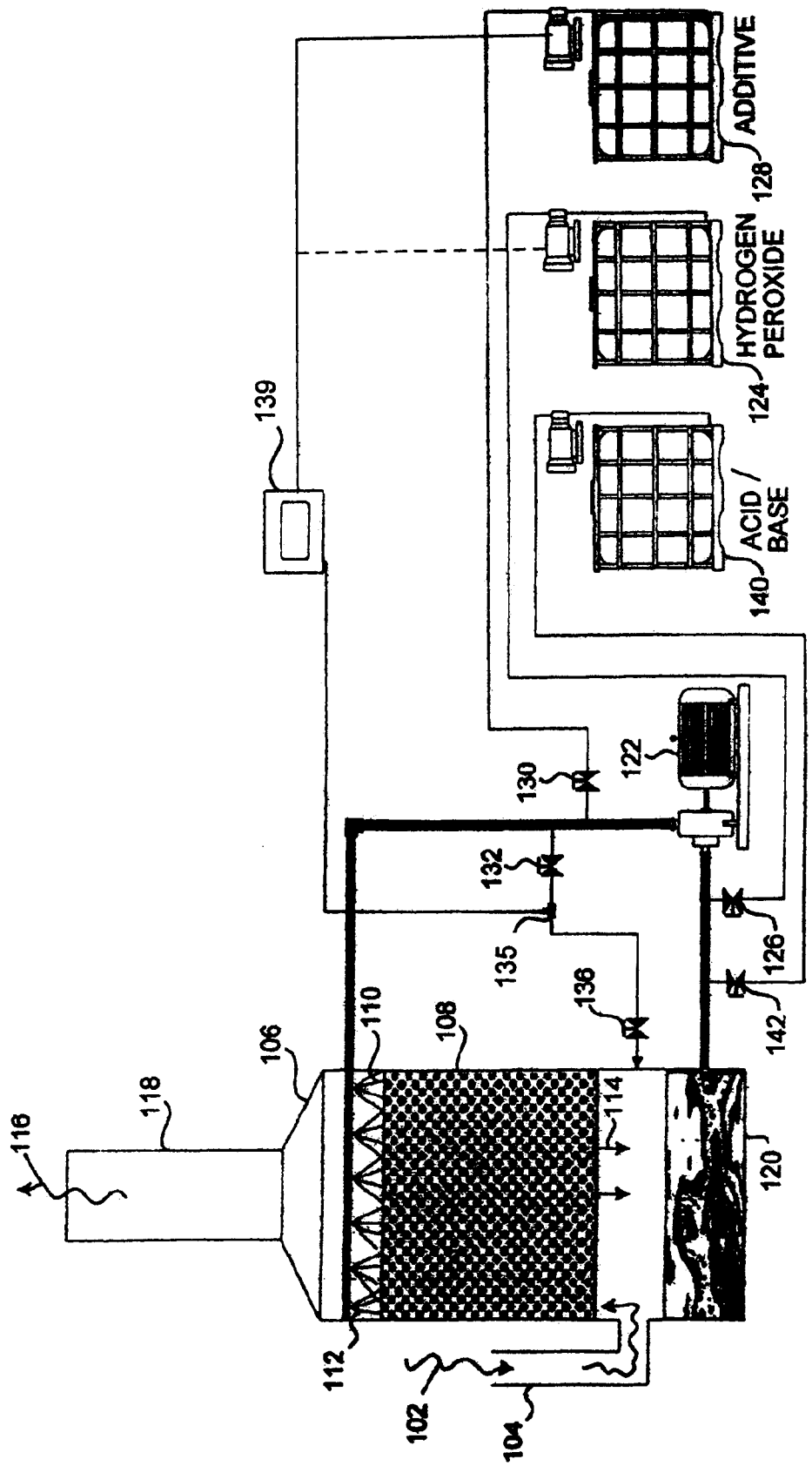
FIG. 1A shows a diagram of another control system for the system of FIG. 1.

FIG. 1A illustrates another control system for the system of FIG. 1. As noted above, the addition of the hydrogen peroxide and the decomposition additive, as well as other additives, is regulated to provide the desired composition in the liquid solution in the scrubber. Similar to the pH control loop discussed above, FIG. 1A shows a probe 135 that is designed to measure a given solution parameter or measurable parameter that can be used to control the addition rate of the hydrogen peroxide or the additives or both. For example, the probe 135 may measure the oxidation-reduction potential of the solution or a particular chemical species, such as a given additive, a species that is indicative of the concentration of the additive, the concentration of gaseous species absorbed by the scrubber, or a combination of these. This probe 135 may be placed in a sidestream similar to the one described above in connection with the pH probe 134. A controller 139 may be used to receive the output from the probe 135 and in response automatically control the addition rate via the pumps that add the hydrogen peroxide from its source container 124 or the additive from its source container 128. In one embodiment, the hydrogen peroxide addition rate may be set at a given, constant value, and the probe 135 and controller 139 would be used to control the addition rate of the decomposition additive (as shown by the solid line between the controller 139 and the source container 128 for the additive). Alternatively, the rate of addition of the decomposition additive may be set at a given, constant value, and the probe 135 and controller 139 would be used to control the addition rate of the hydrogen peroxide (as shown by the dashed line between the controller 139 and the source container 124 for the hydrogen peroxide). It should be appreciated, that separate control loops may be used for the hydrogen peroxide and the additive, respectively, depending upon the type of probe used and the solution parameter that is being measured. It should also be appreciated that a pH control loop may be used in combination with the control loop shown in FIG. 1A.

Figure 1B:
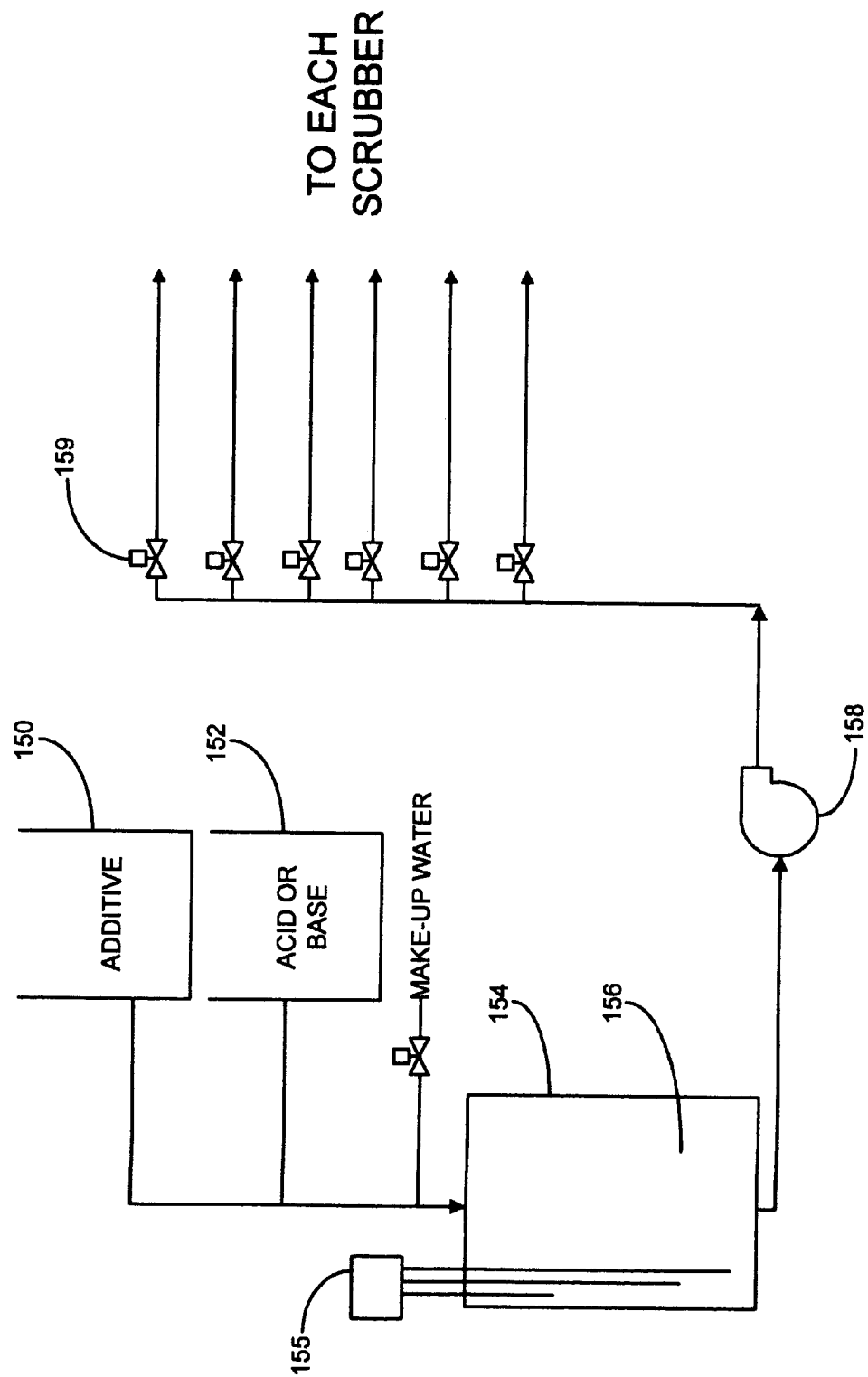
FIG. 1B shows a diagram for a system for adding additive(s) and acid or base for pH control to one or more gas/liquid contactors or scrubbers.

FIG. 1B shows a diagram for a system for adding additive(s), such as the decomposition additive and other additives described above, and acid or base for pH control to one or more gas/liquid contactors or scrubbers. As noted above, a system may include more than one scrubber/reservoir combination. In the system shown in FIG. 1B, each source container for each additive and for acid or base (e.g., a ferrous sulfate source container 150 and a source container for acid or base for pH control 152) is fluidly connected to a single feed tank 154. The feed tank 154 may have a level controller 155 that is used to control the addition rate of the additive(s), the acid or base, the make-up water, or a combination of these to the feed tank 154. Of course, the concentration of the additive(s) and acid or base in their respective source containers 150, 152 will need to be accounted for in determining their addition rate to the feed tank 154 or visa versa. It should be appreciated that while FIG. 1B is shown for use in adding additives and acid or base to multiple scrubbers, the use of a single tank 154 for mixing additives and acid or base may be used for systems having only one scrubber/reservoir as well.

The feed tank 154, accordingly, comprises a solution 156 of the various additives fed to it and any desired acid or base for pH control of the recirculating solution for each scrubber. Depending upon the additive or combination of additives used, the chemical effect of the addition of acid or base to the feed tank 154 on any such additives needs to be considered to ensure that the desired chemical effect of the additives would not be adversely altered before its addition to the scrubbers.

The feed tank 154 is fluidly connected to a distribution pump 158 that is fluidly connected to each scrubber's recycle line or sidestream (not shown) via a flow control valve 159 at the desired location along each recycle line or sidestream. One desired location for distributing the solution 156 from the feed tank 154 to each recycle line or sidestream may be downstream of each scrubber's recycle line or sidestream pump, as shown, for example, by the relative location of the additive addition via the valve 130 to the pump 122 in FIG. 1. It should be appreciated, however, that the point of addition to each scrubber may vary from scrubber to scrubber and may include points other than the recycle line or other or additional points along the recycle line. In other words, the solution 156 may be added to different locations along each scrubber's recycle line or at different points for each scrubber, such as each scrubber's reservoir.

The flow control valve 159 may be any flow control valve, including a valve having precise control over the flow rate that passes through it, such as an analog valve, or, alternatively, an on/off valve. In either case, the flow control valve 159 may be controlled based upon a certain solution parameter measured, either on a continuous, semi-continuous or periodic, or manual basis, in each scrubber's recycle line or in each scrubber's reservoir. The solution parameter measured may be the concentration of any chemical species or solution specific measurement that provides information that can be used to determine whether to add additional additive(s). The solution parameter may include such parameters as pH, oxidation reduction potential, the concentration of the decomposition additive or a particular chemical species indicative of the concentration of the additive, the concentration of gaseous species absorbed by the scrubber, or a combination of these as further described below. In some embodiments, the measurement of the solution parameter is done automatically either on a continuous, semi-continuous or periodic basis, and the results of such measurement are used to automatically control the flow control valve 159. Of course, the required feed rate of the solution 156 in the feed tank 154 to each scrubber will be based upon each particular application, including, for example, the particular noxious components to be removed, the amount of gas being treated, and the operating conditions of each scrubber (e.g., the recirculation rate of the aqueous hydrogen peroxide composition through the scrubber) and the concentration of the various components in the solution 156 in the feed tank 154.

In operation, the addition rate of the solution 156 from the feed tank 154 to each recycle line or sidestream of each scrubber may be controlled in various manners. In some embodiments, the addition of this solution 156 is controlled by the pH control loop on each recycle line as described above in connection with FIG. 1. In this case, a separate pH controller would be used for each scrubber and would control a respective flow control valve 159 to determine the flow rate of solution 156 from the feed tank 154 to that scrubber's recycle line. In other embodiments, different solution parameters could be monitored and used to control the addition rate of the solution 156 from the feed tank 154 by the flow control valve

159. As noted above, oxidation reduction potential, the concentration of the decomposition additive or a particular chemical species indicative of the concentration of the additive, the concentration of gaseous species absorbed by the scrubber, or a combination of these could be monitored and used to control the addition rate of the solution 156.

As described above, depending upon the specific application, the concentrations of the additive(s) and the acid or base in the solution 156 can be adjusted so that the appropriate amount of each is fed to each scrubber. In addition, the relative concentrations in the solution 154 in the feed tank 156 may need to be adjusted for each specific application so that the appropriate amount of each additive and acid or base can be fed to each scrubber. This can be accomplished by adjusted the concentration of the additives and the acid or base in their respective source containers 150, 152. Further, these concentrations must be adjusted to be consistent with each scrubber's and the overall system water balance.

It should be appreciated that using a flow control valve 159 allows for more precise control of the flow rate to each scrubber, as opposed to a simple on/off valve, in combination with monitoring either pH or another solution parameter provides for better control of the solution chemistry and removal of the noxious and odorous components. Particularly by monitoring the pH or another solution parameter in the recycle stream, as shown in FIGS. 1 and 1A, the composition of the solution that is contacting the gas stream is more well known than, for example, monitoring the solution in the reservoir. Further, by adding the additive and/or acid or base directly to the recycle stream based upon the results of monitoring of the solution in the recycle stream allows the recycle stream chemistry to be properly controlled or adjusted just prior to entering the scrubber. This allows for more optimal control of the removal of the noxious and odorous components.

Optionally, any make-up water required for each reservoir may also be added to the feed tank 154. In this case, the dilution effect of any water added to the feed tank 154 must be taken into account so that the desired amount of each additives and acid or base are ultimately added to each recycle line. In addition, the water make-up needs of each reservoir, to the extent that they are different, must be taken into account. In other words, a water balance must be achieved for the overall system, which will also impact the amount of water in the feed tank 154, as discussed above. Alternatively, make-up water may be added directly to each scrubber's reservoir.

In the system as shown in FIG. 1B and as described above, the hydrogen peroxide can be added from separate source containers directly to the recycle line or sidestream of each scrubber, or a single source container can be used with a distribution system to each recycle line or sidestream of each scrubber. Preferably, the hydrogen peroxide would be added upstream of each scrubber's recycle or sidestream pump, such as shown by the relative location of the additive addition via the valve 126 to the pump 122 in FIG. 1. In all cases, a control valve would be used to monitor and regulate the flow of hydrogen peroxide for each scrubber. The control of such a control valve could be based upon the removal efficiency of each scrubber or it could be based upon the relative addition rate of the decomposition additive to the recycle line of each scrubber.

As an alternative to FIG. 1B, each source container of additive or acid or base may be separately connected to a separate corresponding main header line that is fluidly connected to each recycle line or sidestream of each scrubber at the desired location along the recycle line or sidestream (not shown). In other words, the source container for each additive would be separately connected to each scrubber via its own main header line. As described above, one desired location for the addition of additives that catalyze the decomposition of hydrogen peroxide to each scrubber may be downstream of each scrubber's recycle line or sidestream pump, as shown, for example, by the relative location of the additive addition via the valve 130 to the pump 122 in FIG. 1. It should be appreciated, however, that the desired location for the addition of other additives may vary according to the particular additive used. For example, as described above, in using ozone as the catalyst, an air/ozone mixture may be added directly to a regenerative turbine pump in the recycle line or sidestream of each scrubber. Alternatively, a regenerative turbine pump may be used to pump hydrogen peroxide from its source container to a main header line that is fluidly connected to each scrubber, wherein an air/ozone mixture is added to that regenerative turbine pump rather than to each pump in each recycle line or sidestream.

Desired locations for the addition of acid or base for pH control in this alternative embodiment include upstream of each scrubber's recycle or sidestream pump, such as shown by the relative location of the additive addition via the valve 126 to the pump 122 in FIG. 1 and in some embodiments upstream of the addition point for the hydrogen peroxide also as shown in FIG. 1. In this alternative, the hydrogen peroxide may be added, for example, in the same manner as described above in connection with FIG. 1B.

Generally, it should be appreciated that the addition of the various components comprising the aqueous hydrogen peroxide composition may be added at various locations throughout the scrubber system and are not limited to those described in the above embodiments. For example, the hydrogen peroxide and other additives may be added at other locations in the recycle line or sidestream or directly to the reservoir or tank, although some of these locations are more desirable than others, as discussed in the embodiments above.

Figure 1C:
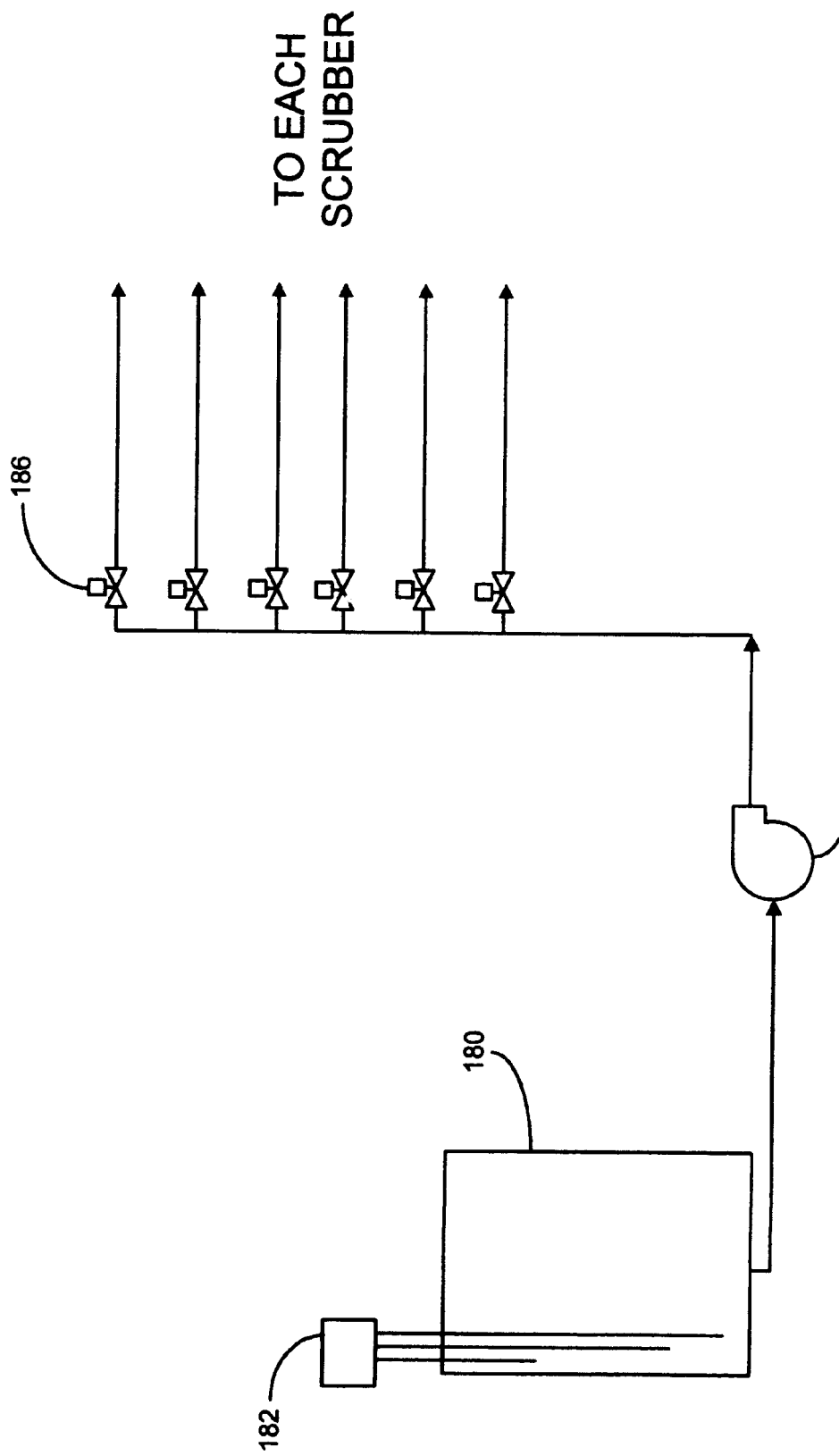
FIG. 1C shows a diagram for a system for adding an oxidizer to one or more gas/liquid contactors or scrubbers.

FIG. 1C shows a diagram for a system for adding an oxidizer to one or more gas/liquid contactors or scrubbers. A feed tank 180 is used to hold the oxidizer, which may include hydrogen peroxide or another oxidizer such as chlorine gas, sodium hypochlorite, hypobromous acid, chlorine dioxide, hydrogen peroxide, peroxy acids, ozone, and permanganate. The feed tank 180 may also have a level controller 182 that functions to provide an alert when the tank level is low and additional hydrogen peroxide and/or water is required. It should be appreciated that certain additives may also be added to the feed tank 180 provided they are chemically compatible with an oxidizer, such as hydrogen peroxide, so that their chemical activity is not lost prior to being added to the scrubber. It should also be appreciated that the system of FIG. 1C can be used in conjunction with the system of FIG. 1B and further in conjunction with a pH control loop.

The feed tank 180 is fluidly connected to a distribution pump 184 that is fluidly connected to each scrubber's recycle line or sidestream (not shown) via a flow control valve 186 at the desired location along each recycle line or sidestream. One desired location for distributing the oxidizer from the feed tank 180 to each recycle line or sidestream may be upstream of each scrubber's recycle line or sidestream pump, as shown, for example, by the relative location of the additive addition via the valve 126 to the pump 122 in FIG. 1. It should be appreciated, however, that the point of addition to each scrubber may vary from scrubber to scrubber and may include points other than the recycle line or other or additional points along the recycle line. In other words, the oxidizer may be added to different locations along each scrubber's recycle line or at different points for each scrubber, such as each scrubber's reservoir.

In operation, the addition rate of the oxidizer from the feed tank 180 to each recycle line or sidestream of each scrubber may be controlled in various manners. In some embodiments, the addition of the oxidizer is simply set a given feed rate for each scrubber using the flow control valve 186. In other embodiments, different solution parameters could be monitored and used to control the addition rate of the oxidizer from the feed tank 180 by the flow control valve 186. As noted above, oxidation reduction potential, the concentration of the decomposition additive or a particular chemical species indicative of the concentration of the additive, the concentration of gaseous species absorbed by the scrubber, or a combination of these could be monitored and used to control the addition rate of the oxidizer from the feed tank 180. Of course, the concentration of the oxidizer will need to be accounted for in determining its addition rate to each scrubber or visa versa.

It should be appreciated that using a flow control valve 186 allows for more precise control of the flow rate to each scrubber, as opposed to a simple on/off valve. Particularly, by monitoring a given solution parameter in the recycle stream, as shown in FIGS. 1 and 1A, the composition of the solution that is contacting the gas stream is better known than, for example, monitoring the solution in the reservoir. Further, by adding the oxidizer directly to the recycle stream based upon the results of monitoring of the solution in the recycle stream allows the recycle stream chemistry to be properly controlled or adjusted just prior to entering the scrubber. This allows for more optimal control of the removal of the noxious and odorous components. However, it should be appreciated that in one embodiment it is desirable to simply set the addition rate of the oxidizer to a given, constant value and to adjust the addition rate of any additives (e.g., a decomposition additive in the case of using hydrogen peroxide as the oxidizer) accordingly.

Optionally, any make-up water required for each reservoir may also be added to the feed tank 180 (not shown). In this case, the dilution effect of any water added to the feed tank 180 must be taken into account so that the desired amount of each additives and acid or base are ultimately added to each recycle line. In addition, the water make-up needs of each reservoir, to the extent that they are different, must be taken into account. In other words, a water balance must be achieved for the overall system, which will also impact the amount of water in the feed tank 180, as discussed above. Alternatively, make-up water may be added directly to each scrubber's reservoir.

As mentioned above, the liquid effluent produced by the present invention also offers advantages to influent to the wastewater treatment process. For example, when using ferrous sulfate as the additive to catalyze the decomposition of the hydrogen peroxide, the gas/water scrubber water, e.g., the liquid effluent, can be evacuated to a wastewater treatment facility, for example, by dumping the entire liquid content of the reservoir or by continuous overflow of from the reservoir or recycle line or sidestream, and this stream will have been effectively "pretreated" by cationic ferric hydroxide complexes that offer effective colloidal charge neutralization as well as the ability to adsorb wastewater constituents into its floc matrix. The addition of a charge neutralizing/adsorption species is always an added cost at the wastewater treatment plant. By use of the present invention that cost is eliminated or greatly reduced.

Figure 2:
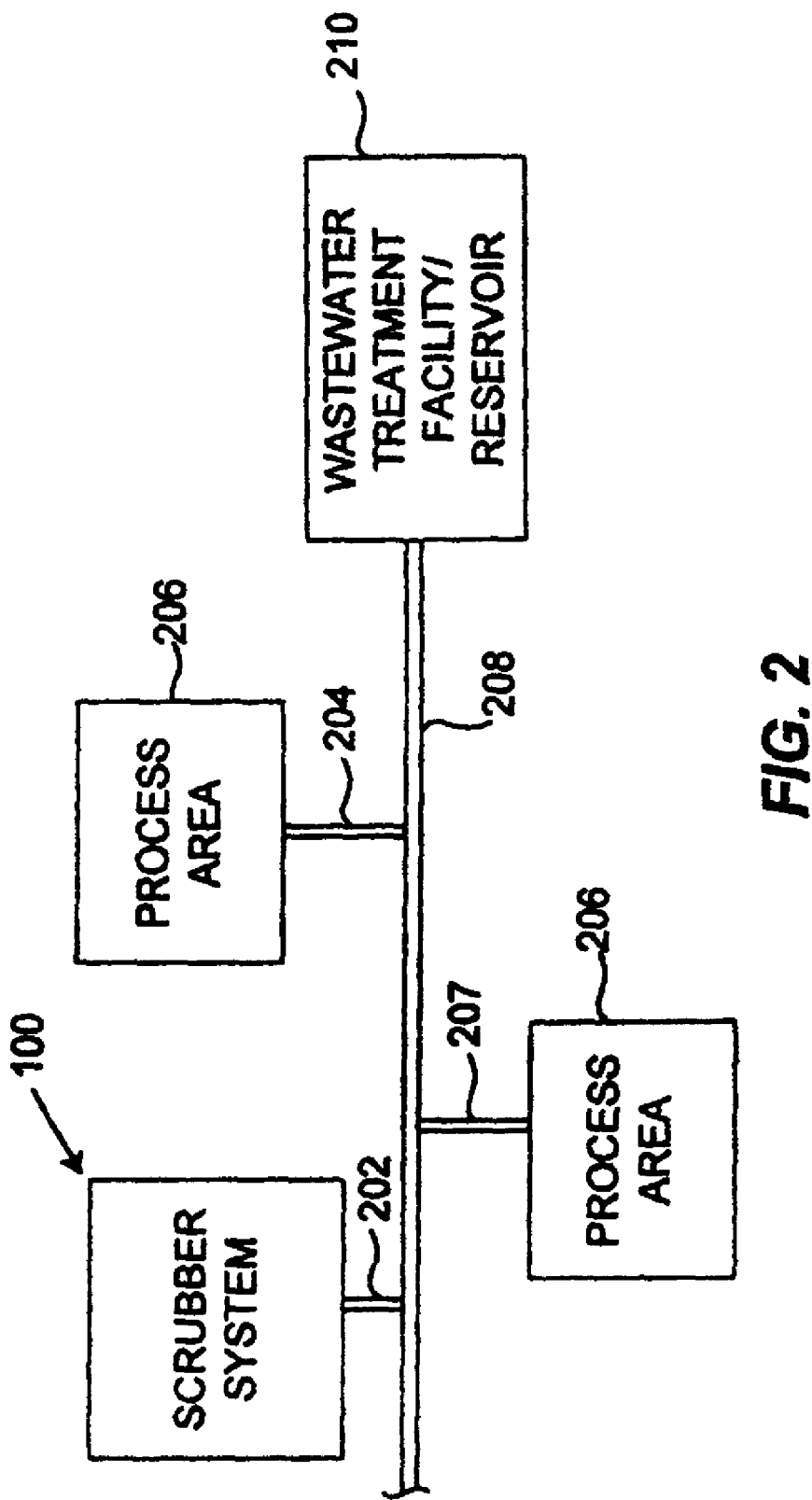
FIG. 2 shows the system of FIG. 1 within a wastewater effluent system of a processing plant illustrating the pretreatment properties of the present invention on the waste treatment facility according to one embodiment of the present invention.

FIG. 2 shows the system of FIG. 1 within a wastewater effluent system of a processing plant illustrating the pretreatment properties of the present invention on the waste treatment facility according to one embodiment of the present invention. In FIG. 2, liquid effluent is discharged from the system 100 earlier described with reference to FIG. 1, for example, through a wastewater pathway 202. As earlier described, the liquid effluent may be discharged by dumping the reservoir or by continual overflow of the liquid effluent from the reservoir. The wastewater pathway 202 may merge with other wastewater pathways 204 exiting from other process areas 206 in the processing plant, for example, wash and rinse waters, chicken feather processing waters, rendering cooker waters, etc. These wastewater pathways 202, 204 eventually converge into one or more wastewater pathways 208 that discharge into one or more large reservoirs in a wastewater treatment facility 210.

When the liquid effluent enters the reservoir at the wastewater treatment facility 210, the liquid effluent is effectively "pre-treated". The liquid effluent contains metal hydroxide complexes, for example, cationic ferric hydroxide complexes, that offer effective colloidal charge neutralization, as well as provide for adsorption of wastewater constituents into its floc matrix. While some of the complexes are utilized by the components of the liquid effluent, a residual amount of these complexes are also available to the other wastewater effluent in the reservoir of the wastewater treatment facility. As wastewater treatment facilities typically purchase additives to accomplish these results, the addition of these charge neutralizing and adsorption species eliminates or greatly reduces any costs incurred by the waste treatment facility.

The present invention has been described above with reference to removal of odor and/or noxious components from an atmospheric effluent in which the oxidized odor and/or noxious components are oxidized during contact with an aqueous hydrogen peroxide composition to produce a substantially non-odor offensive, environmentally acceptable by-product that is solubilized in or adsorbed onto the aqueous hydrogen peroxide composition to form a liquid effluent, and the advantages of such a system provided to wastewater treatment processes. The present invention also has application in other areas of processing plants as an effective biocide, especially in areas related to aqueous food transport flumes.

Food primary and secondary processing involves the handling of large amounts of organic materials. As a result of the amount of organics being processed, biological activity is inevitable. In fruit and vegetable processing, large amounts of water are used to wash and transport food through the various processing steps. Because of the buildup of organic matter, the transport and wash waters are very prone to biological growth, as well as accumulation of toxic organic materials such as herbicides and pesticides. A need exists to provide microbial control of these waters without imparting further toxic products to the aqueous food contact streams. Also needed is an economical method for eliminating or reducing the buildup of toxic herbicides and pesticides in the food transport system.

Attempts in the art have been made utilizing oxidizing compounds such as chlorine gas, sodium hypochlorite, hypobromous acid, chlorine dioxide, hydrogen peroxide, peroxy acids, ozone, and permanganate. While some are effective in limiting microbial growth, either toxic by-products, cost, or inefficiencies are limiting factors.

Particularly, the use of chlorine and chlorine dioxide, while effective antimicrobial agents, has come under environmental scrutiny due to the toxic by-products it produces. When contacted with amines, toxic chloramines are formed, as well as trihalomethane compounds, which are now prevalent in most ground waters in the United States. Chlorine-based technologies also use large quantities of these materials, as they are rapidly consumed by the high organic loading of the aqueous media before they can impart antimicrobial properties. Hypobromous acid produced by the decomposition of sodium bromide by chlorine has been used with some success, but it too is affected by high organic loading and the chlorine substrates, which, while reduced, still impart the same toxicities as hypochlorous acid.

Hydrogen peroxide has been used with limited success. Hydrogen peroxide is a slow reacting compound with known antimicrobial properties. The reaction rates are too slow for effective, cost advantageous microbial control. Peroxy acids such as peracetic acid have proven to be effective antimicrobial compounds in aqueous systems. Peracids are usually manufactured by the combination of hydrogen peroxide, acetic acid, and inorganic acid catalyst, and various wetting and sequestering agents. Peracetic acid is normally provided in 5 to 15% peracetic acid concentrations. These peracid compounds contain large amounts of the manufacturing precursors, such as hydrogen peroxide, and acetic acid. These peroxy acid materials have a strong pungent odor and residual acetic acids are toxic by ingestion or exposure at 10 ppm in misted form. Peroxy acids are also limited in use by the high costs that are associated with it. Ozone has found limited use in aqueous food transport and processing streams. Ozone is an effective biocide and its high electronegativity is capable of breaking down selected organic compounds. Ozone is associated with extremely high capital investments cost, and the efficiency is limited by poor transfer coefficients from the generated ozone gas phase to the liquid media being treated.

Use of the present invention, however, in which an aqueous hydrogen peroxide composition of hydrogen peroxide decomposed by ozone is contacted with the transport waters, results in an effective biocide. This allows sterilization of food transport waters with no toxic by-products. Further, in food transport flumes, regulation of the ozone can also break down accumulated pesticide and herbicide compounds from fruit and vegetable washing into simple non-toxic carboxylic acids. Accordingly, this technology offers significant cost and efficiency advantages over current technologies.

EXAMPLES

The following examples describe specific aspects of the present invention to illustrate the invention and aid those of skill in the art in understanding and practicing the invention. The examples should not be construed as limiting the present invention in any manner.

Example #1

A 1000 ml sample of chicken feather processing scrubber water having a pH of 5.5 due to sulfuric acid addition in the scrubber reservoir was evaluated. The sample had an intense odor after treatment with chlorine dioxide. The sample was treated concurrently with 300 ppm of hydrogen peroxide (50% solution) and 100 ppm ferrous sulfate (38% solution). The reaction was instantaneous, and there was no detectable odor, other than a slight chlorine smell.

Example #2

A 1000 ml sample from a rendering cooker was adjusted to pH 5.5 with sulfuric acid. The sample had a very intense odor. The sample was treated concurrently with 300 ppm of hydrogen peroxide (50% solution) and 100 ppm ferrous sulfate (38% solution). The reaction was instantaneous, and the odor was eliminated within 15 seconds. The sample was then undisturbed for 48 hours, and there was no re-occurrence of any odor.

Example #3

A five gallon sample from a rendering cooker was adjusted to pH 5.5. The sample was recirculated at 10 gpm through a Burks regenerative turbine pump throttled by pinch valve assembly to 100 psi. Hydrogen peroxide was introduced into the suction line at 300 ppm. Ozone as a 6% gas stream generated by a corona discharge type ozonater on dried air was added into the air inlet for the Burks pump (suction side). The ozone dose was 10 ppm as ozone. The sample was recirculated for 2 minutes, and odors were completely neutralized. The sample was then un-aearated and undisturbed for 48 hours, and there was no re-occurrence of any odor.

Example #4

A trial was performed at a mixed proteins rendering plant that used chlorine dioxide in a scrubber to reduce VOC emissions by 88%. In this system, the pH was reduced to pH 5.5 with sulfuric acid. 300 ppm of hydrogen peroxide (50% solution) and 100 ppm ferrous sulfate (38% solution) were added concurrently. As a result, VOC emissions were reduced by 96%.

In the above examples, odor reduction was measured using the sense of smell and VOC emission measurements using standard emission detectors. It will be appreciated that various other devices and measurement techniques may also be used that conform to standard practices as may be required for a particular processing industry.

Example #5

A pilot plant test using hydrogen peroxide decomposed by ozone was conducted to evaluate microbiological control. The test or run was performed using 100 gallons and a Pennsylvania apple wash/transport flume with the following characteristics: BOD=900 ppm, COD=2100 ppm, and a significant amount of large organic matter. The material was recirculated for 36 hours and the following data was collected: bio count via dip slide=109, filtered BOD (0.45 micron)=685 ppm, filtered COD (0.45 micron)=1725 ppm.

300 ppm hydrogen peroxide (50% solution) was added, and ozone was added at 10 ppm into a regenerative turbine pump used to recirculate solution. When the addition of hydrogen peroxide and ozone was completed the addition was stopped. The following bio count in colonies was observed: @ t=4 min bio count=102, @ t=10 min bio count=none detected, @ t=8 hours bio count=none detected, @ t=12 hours bio count=10, and @ t=18 hours bio count=102. Additional data included: filtered BOD=210 ppm and filtered COD=720 ppm.

As can be seen by this test, microbial control was excellent with good sustained kill of biopopulation. The lowering of the COD showed decomposition of organic material in the sample water. Analysis for toxicity indicated a sharp drop.

Although the foregoing invention has been described in some detail to facilitate understanding, it will be apparent that certain changes and modifications may be practiced within the scope of the appended claims. Accordingly, the described embodiment is to be considered as illustrative and not restrictive, and the invention is not to be limited to the details given herein, but may be modified within the scope and equivalents of the appended claims.

What is claimed is:

1. A gas/liquid contactor for removing an odorous or noxious component from a gas stream, comprising:
   a gas/liquid contactor for receiving a gas stream comprising at least one odorous or noxious component;
   a liquid stream to which hydrogen peroxide and a hydrogen peroxide decomposition additive have been added;
   a recycle line for recycling said liquid stream through said gas/liquid contactor;
   a probe for measuring a measurable parameter of said liquid stream; and
   a feed tank comprising a solution of an acid or a base and said hydrogen peroxide decomposition additive and fluidly connected to said recycle line to add said acid or said base and said hydrogen peroxide decomposition additive to said liquid stream in said recycle line in response to a measurement of said measurable parameter by said probe.

2. The gas/liquid contactor of claim 1, wherein said gas/liquid contactor comprises a packed tower.

3. The gas/liquid contactor of claim 1, wherein said liquid stream comprises a chelating agent for increasing the solubility of said hydrogen peroxide decomposition additive.

4. The gas/liquid contactor of claim 1, wherein said measureable parameter is pH of said liquid stream.

5. The gas/liquid contactor of claim 1, wherein said measureable parameter is oxidation reduction potential of said liquid stream.

6. The gas/liquid contactor of claim 1, wherein said hydrogen peroxide decomposition additive comprises ferrous sulfate.

7. The gas/liquid contactor of claim 1, wherein said hydrogen peroxide decomposition additive comprises ferric sulfate.

8. A apparatus for removing an odorous or noxious component from a gas stream, comprising:
   a plurality of gas/liquid contactors for contacting a gas stream comprising at least one odorous or noxious component with a liquid stream to which hydrogen peroxide and a hydrogen peroxide decomposition additive have been added;
   a plurality of recycle lines, each for recycling the liquid stream through a corresponding one of said plurality of gas/liquid contactors;
   a plurality of probes for measuring a solution parameter of the liquid stream being used in a corresponding one of said gas/liquid contactors;
   a first feed tank comprising an acid or a base;
   a second feed tank comprising a hydrogen peroxide decomposition additive;
   a third feed tank fluidly connected to said first feed tank and said second feed tank for receiving said acid or said base from said first feed tank and said hydrogen peroxide decomposition additive from said second feed tank to produce a mixture of said acid or said base and said hydrogen peroxide decomposition additive in said third feed tank, wherein said third feed tank is fluidly connecting to each one of said plurality of recycle lines to feed said mixture to a corresponding one of said plurality of recycle lines in response to a measurement of the solution parameter of liquid stream that passes through said corresponding one of said plurality of recycle lines by a corresponding one of said plurality of probes.

9. The apparatus of claim 8, wherein said plurality of gas/liquid contactors are in series.

10. The apparatus of claim 8, wherein said plurality of gas/liquid contactors are in parallel.

11. The apparatus of claim 8, further comprising a third feed tank for holding the hydrogen peroxide, wherein said third feed tank is fluidly connected to each of said recycle lines to allow the hydrogen peroxide to pass to the liquid stream in any one of said recycle lines.

12. The apparatus of claim 8, further comprising a third feed tank for holding the hydrogen peroxide, wherein said third feed tank is fluidly connected at a plurality of locations along each of said recycle lines to allow the hydrogen peroxide to pass to the liquid stream in any one of said recycle lines at each of said plurality of locations along each of said recycle lines.

13. The apparatus of claim 1, wherein said liquid stream comprises at least one additional additive.

14. The apparatus of claim 13, wherein said at least one additional additive catalyzes the decomposition of hydrogen peroxide.

15. The apparatus of claim 13, wherein said at least one additional additive comprises a nonionic wetting agent.

16. The apparatus of claim 13, wherein said feed tank comprises said at least one additional additive.

17. The apparatus of claim 8, wherein said second feed tank further comprises at least one additional additive.

18. The apparatus of claim 17, wherein said at least one additional additive catalyzes the decomposition of hydrogen peroxide.

19. The apparatus of claim 17, wherein said at least one additional additive comprises a nonionic wetting agent.

20. The apparatus of claim 17, wherein said at least one additional additive comprises a chelating agent for increasing the solubility of said hydrogen peroxide decomposition additive.

* * * * *